(12) United States Patent
Flaxmeier et al.

(10) Patent No.: US 7,988,662 B2
(45) Date of Patent: Aug. 2, 2011

(54) METAL ELECTRODE

(75) Inventors: Erik Flaxmeier, Kalsfeld (DE); Ralf Steiner, Pforzheim (DE); Wolfgang Müller, Mössingen (DE)

(73) Assignee: Admedes Schuessler GmbH, Pforzheim (DE)

( * ) Notice: Subject to any disclaimer, the term of this patent is extended or adjusted under 35 U.S.C. 154(b) by 1242 days.

(21) Appl. No.: 10/534,594

(22) PCT Filed: Nov. 11, 2003

(86) PCT No.: PCT/EP03/12600
§ 371 (c)(1),
(2), (4) Date: Nov. 21, 2005

(87) PCT Pub. No.: WO2004/043279
PCT Pub. Date: May 27, 2004

(65) Prior Publication Data
US 2006/0129143 A1  Jun. 15, 2006

(30) Foreign Application Priority Data

Nov. 11, 2002 (DE) ................................. 102 52 325
Dec. 6, 2002 (DE) ................................. 102 57 146

(51) Int. Cl.
*A61M 13/00* (2006.01)
(52) U.S. Cl. ........................................................ 604/104
(58) Field of Classification Search .................... 606/41; 604/104, 105; 607/122
See application file for complete search history.

(56) References Cited

U.S. PATENT DOCUMENTS

| 5,400,783 | A | 3/1995 | Pomeranz et al. |
| 5,476,495 | A | 12/1995 | Kordis et al. |
| 5,499,981 | A | 3/1996 | Kordis |
| 5,558,073 | A | 9/1996 | Pomeranz et al. |
| 5,647,870 | A | 7/1997 | Kordis et al. |
| 5,681,280 | A | 10/1997 | Rusk et al. |
| 5,725,525 | A | 3/1998 | Kordis |
| 5,730,128 | A | 3/1998 | Pomeranz et al. |
| 5,823,189 | A | 10/1998 | Kordis |
| 5,893,847 | A | 4/1999 | Kordis |
| 5,904,680 | A | 5/1999 | Kordis et al. |
| 5,928,228 | A | 7/1999 | Kordis et al. |
| 6,036,689 | A | 3/2000 | Tu et al. |
| 6,216,044 | B1 | 4/2001 | Kordis |
| 6,319,251 | B1 | 11/2001 | Tu et al. |
| 6,391,044 | B1 | 5/2002 | Yadav et al. |
| 2001/0029371 | A1 | 10/2001 | Kordis |
| 2002/0103501 | A1 | 8/2002 | Diaz et al. |
| 2002/0138094 | A1 | 9/2002 | Borillo et al. |
| 2002/0198522 | A1 | 12/2002 | Kordis |
| 2003/0060844 | A1 | 3/2003 | Borillo et al. |
| 2004/0153056 | A1 | 8/2004 | Muller et al. |

FOREIGN PATENT DOCUMENTS

WO    WO 01/58382    8/2001

*Primary Examiner* — Michael Peffley
*Assistant Examiner* — Samantha Good
(74) *Attorney, Agent, or Firm* — McDonald Hopkins LLC

(57) ABSTRACT

The invention relates to a spreader structure (10) for introducing into a hollow organ, comprising spreader rods (12), which radiate from a first connection section (14) essentially in the longitudinal direction (36) of the spreader structure (10) up to a second connection section (16), are distributed around the periphery of the spreader structure (10) and can be placed against a wall of a hollow organ by means of radial expansion. The aim of the invention is to provide a spreader structure (10), which is versatile and cost-effective to produce. To achieve this, the spreader rods (10) have at least one zone (22) running in the longitudinal direction, which has a reduced flexural strength in comparison to neighboring zones (20, 24). The invention also relates to the use of said spreader structure, to a spreader device and to a method for positioning a spreader structure.

14 Claims, 4 Drawing Sheets

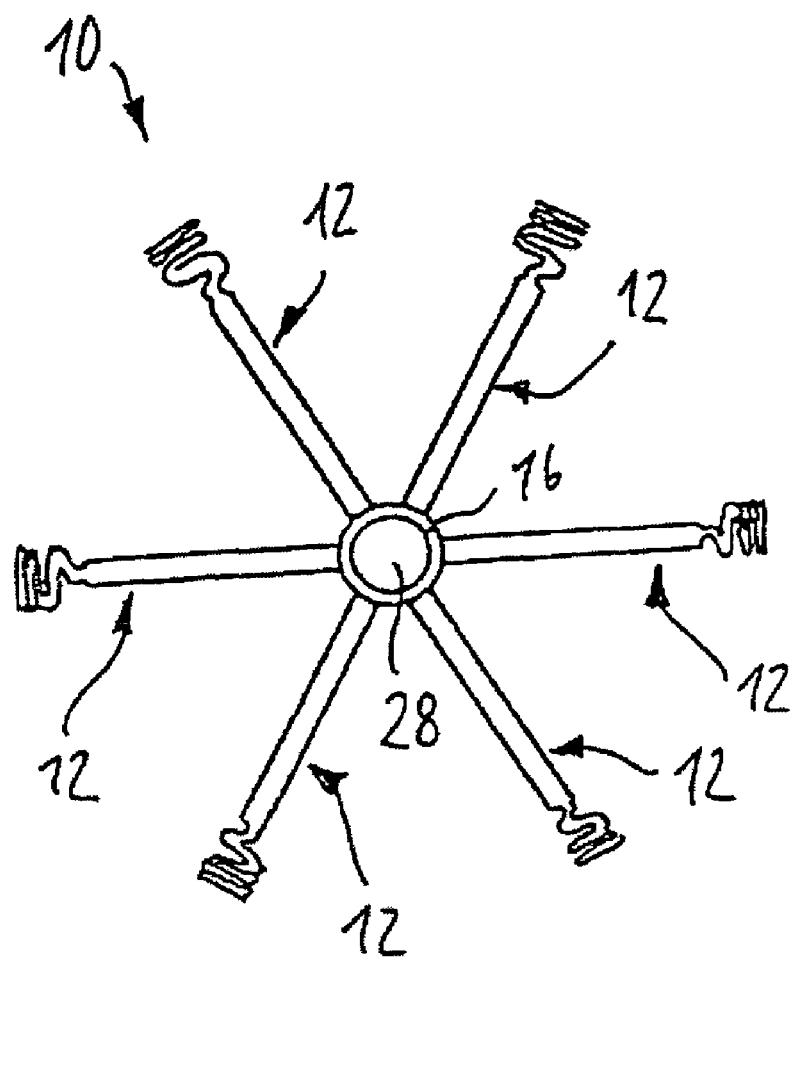

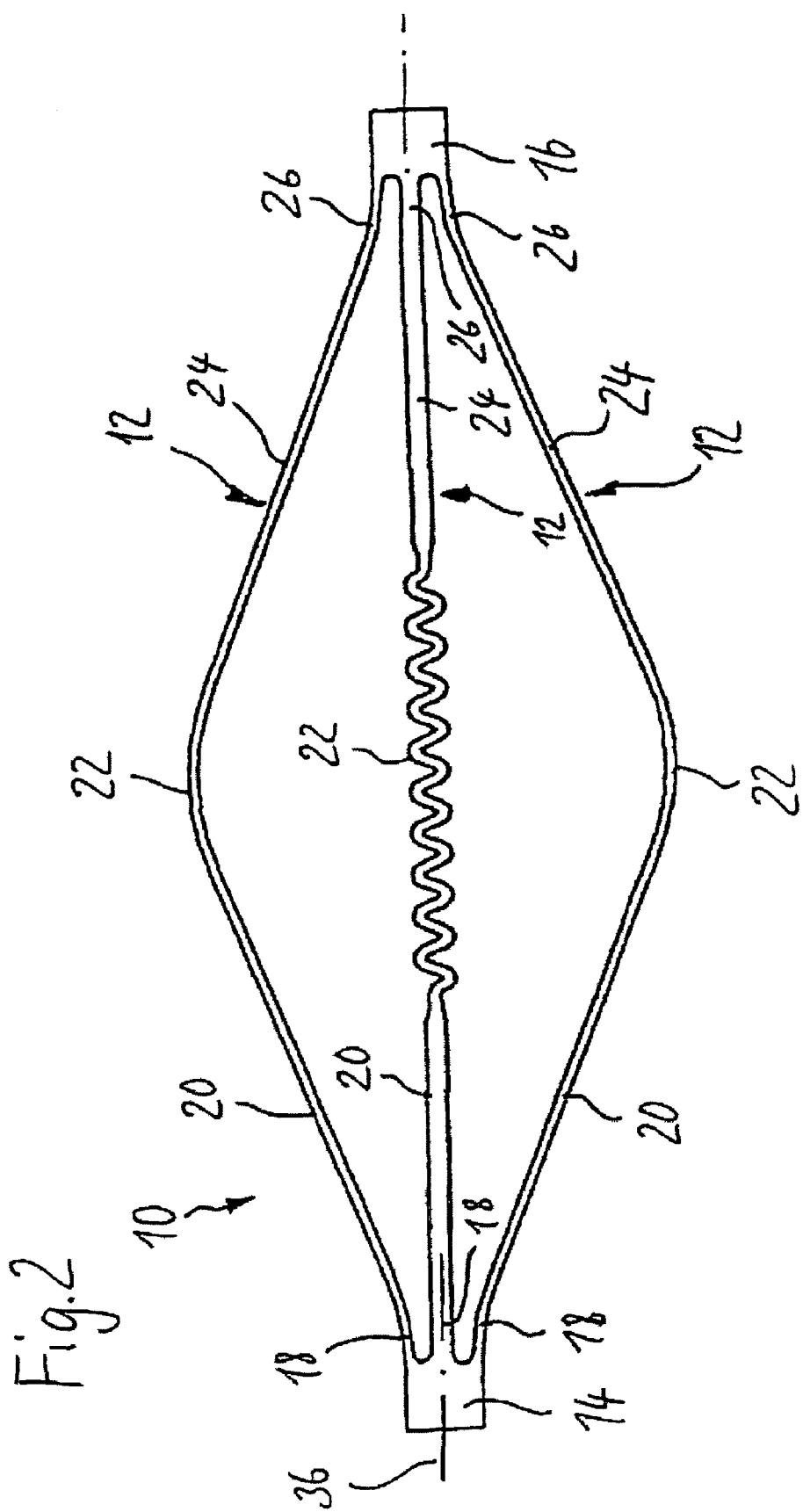

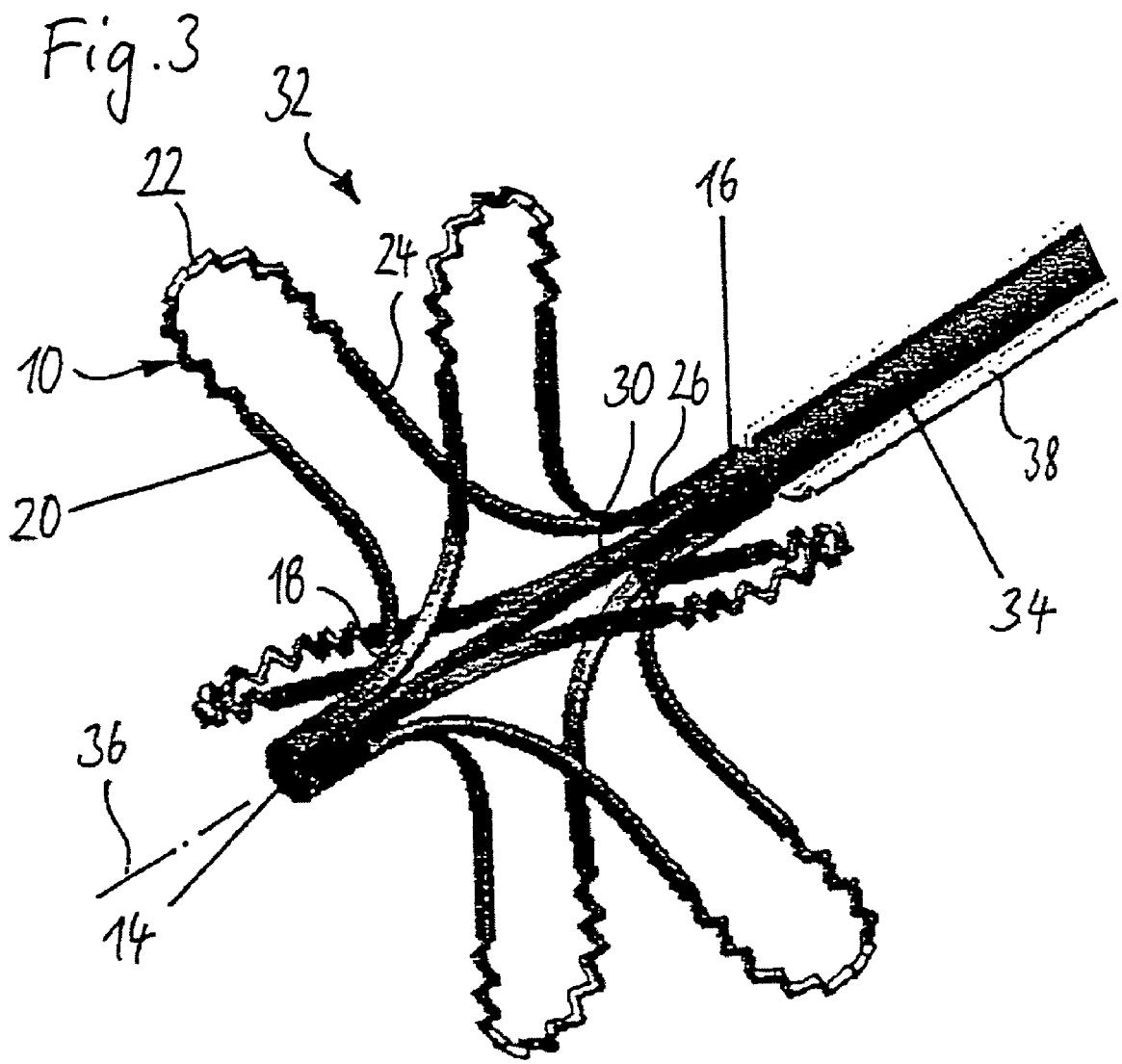

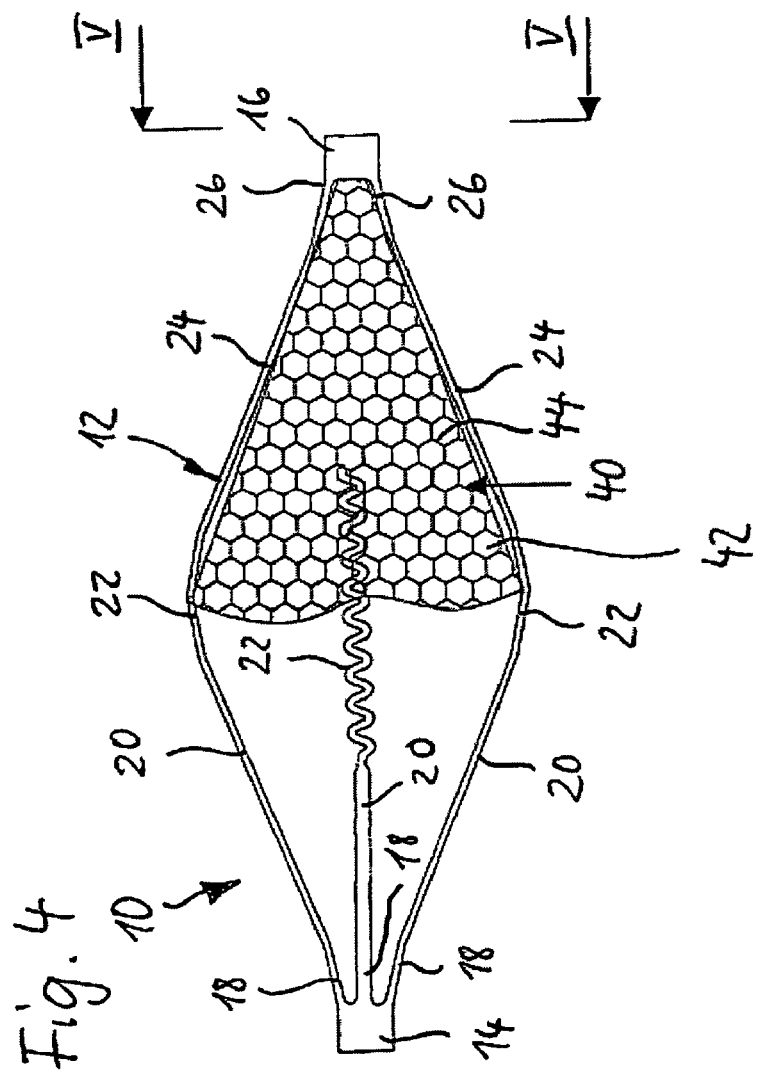
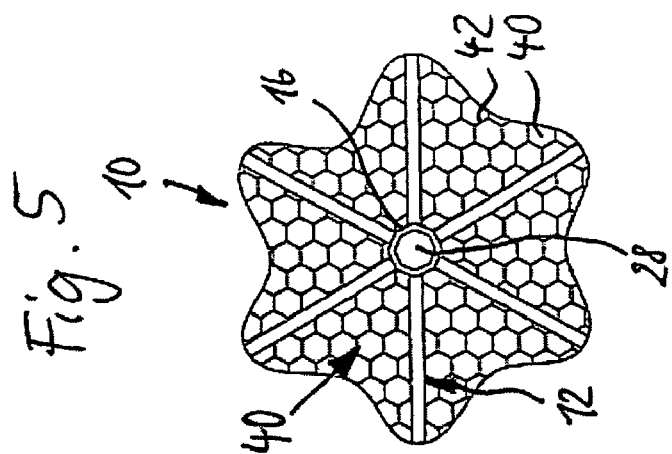

METAL ELECTRODE

This is a U.S. National Stage Application of International Patent Application Ser. No. PCT/EP03/12600 filed Nov. 11, 2003.

The invention relates to a spreader structure for insertion into a hollow organ, comprising spreader rods which extend from a first connecting section substantially in the longitudinal direction of the spreader structure to a second connecting section; these rods are distributed over the circumference of the spreader structure and can be positioned against a wall of the hollow organ by means of radial expansion. The invention also relates to the use of said spreader structure, to a spreader device, and to a method for positioning a spreader structure.

Spreader structures of the type described above are utilized as short-term or permanent implants in a hollow organ, such as the heart, blood vessels, bile ducts, urinary tract, gastrointestinal tract, uterus and cerebral ventricles, in order to trap blood clots (thrombi) or bile duct stones, for example. Several types of thrombosis filters are known which are percutaneously inserted as venous implants through the femoral vein or the jugular vein into the vena cava inferior or the vena cava superior. There, the venous implant is designed to trap blood clots before they can advance to the heart and to prevent a pulmonary embolism. Implants of this type are typically designed with conically extending struts or rods forming a funnel-shaped filter basket.

Self-expanding endoprotheses for keeping duct-like structures open are known as well; these so-called stents are also used in blood vessels. Stents typically are designed to have a hose-like, more or less finely meshed wire weave or wire netting that can be radially expanded by means of the elastic restoring force of the wires thereof.

It is an object of this invention to provide an elongate spreader structure that is versatile and cost-effective to produce.

The present invention achieves this objective by providing a spreader structure and the use thereof, a spreader device, and a method according to claim 1. Further design elements of the invention that provide significant advantages are defined in the dependent claims.

According to the invention, the spreader rods form a body or a spreader structure of an substantially cylindrical design while at rest or in a pretensioned state. While at rest, the spreader structure described in the invention can either have an elongate form and can be expanded from this position of rest, or it can be balloon-shaped while at rest and be compressed into an elongate form from this position of rest.

According to the invention, the spreader rods in this body in particular have at least one area in the longitudinal direction that has less flexural stiffness than adjacent areas.

The spreader structure described in the invention can be very precisely and at the same time very easily compressed or expanded. The areas of reduced flexural stiffness provided by this invention create a predetermined buckling site on the individual rods, where the rod is discretely deformed during contraction or compression and spreading or expanding. According to the invention, this results in the simultaneous formation of a trapping or filter basket, the rods of which can be spread outward particularly far, allowing it to be used in large-volume hollow organs as well.

The spreader structure described in this invention can be used to widen and keep open a vessel; it can also serve as a miniature catch basket for bladder stones, urethroliths, kidney stones, and bile duct stones, for example.

In addition, the ability to discretely expand and contract the spreader structure described in this invention allows foreign bodies to be extracted from the esophagus.

The spreader structure described in this invention thus provides significant advantages both in the field of urology and in gastroenterology.

Finally, the spreader structure described in this invention can also be applied in the area of the peripheral and the coronary circulatory systems. The spreader structure can thus serve as a distal embolic protection or a temporary vena cava filter. In addition, the invention offers a particularly advantageous way of creating a septic occluding system or an occlusion system for aneurysms.

According to the invention, the spreader structure can also be used as a metal electrode for the purpose of introducing heat at a wall of the hollow organ in order to provide treatments such as electrocoagulation.

An additional advantageous feature of the invention is that at least one area that has reduced flexural stiffness compared to the adjacent areas has a reduced cross section. It is best to use one and the same material within the various areas, so that the entire spreader structure can be made of the same material. Non-corrosive metals are particularly well suited, in particular a stainless steel alloy. Tantalum, niobium, cobalt alloys and other materials, such as polymers, biodegradable materials (such as lactic acid-based materials or derivatives) are also particularly useful. This can form an externally expanding spreader structure (in particular of a nickel-titanium alloy and particularly of nitinol) or a self-expanding spreader structure (particularly of a shape memory alloy) can be formed. The material can be electrochemically polished or coated. When the spreader structure is used as a metal electrode, the area with the reduced cross section becomes especially warm, thereby leading to a focused heat infusion at the wall of the hollow organ.

Alternatively or additionally, the at least one area with reduced flexural stiffness can be designed with a non-linear rod section that already has buckles or kinks, causing it to be particularly strongly deformed when the spreader rods are expanded. The non-linear rod section further results in a particularly firm anchoring of the spreader structure described in this invention on the wall of the hollow organ being treated.

According to the invention, a meander-shaped structure is particularly suited for the area with reduced flexural stiffness. A meander-shaped structure is characterized by alternating bent and straight sections that extend on one surface. The surface can be flat or, as in the present case, it can preferably be the surface shell of a circular cylinder. This means that the basic element of the spreader structure of this invention is a tube from which the spreader rods are cut by means of a laser. The meander structure facilitates a particularly easy deformation vertically to the surface of the meanders. It is therefore of particular advantage if the surface of the meanders forms a tangent plane to the circumference of the spreader structure.

For the area with reduced flexural stiffness described in the invention, a wave form or zigzag form is particularly suited. The wave form is characterized by successive, substantially alternating curved sections, while the zigzag form is characterized by successive, substantially straight sections that abut at point-like buckle sites.

In order to achieve a discrete deformation of the spreader rods in defined directions, it is further of advantage if the cross section of the area of reduced flexural stiffness is square-shaped.

It is particularly advantageous if the connecting sections take the form of central hubs in the area of the longitudinal axis of the spreader structure. The connecting sections thus form a "point" at each end of the spreader structure, in particular at the distal end, thereby facilitating the insertion, movement and removal of the spreader structure in the hollow organ.

In addition, an opening is provided in at least one of the connecting sections, through which a central rod can be inserted up to the second connecting section. By means of the central rod, the spreader structure described in this invention can be expanded and compressed by reducing or increasing, respectively, the distance along the longitudinal axis of the spreader structure between the connecting sections.

It is particularly advantageous to make the connecting sections substantially cylindrical, thereby evenly distributing the spreader rods around the circumference thereof and creating a uniformly sturdy structure over the entire circumference of the spreader structure.

In the starting position of the spreader structure described in this invention, it is of advantage if the spreader rods have a first section that is radially curved outward and is followed by an substantially straight second section, each radiating from a connecting section. At the precurved first section, the spreader rods buckle discretely when the spreader structure is expanded or compressed, respectively, while the substantially straight second sections transfer the expanding force as a compressive force to the area of reduced flexural stiffness described in the invention. The substantially straight sections thus do not substantially bend or buckle in the spreader structure described in the invention, resulting in a particularly large radial widening of the spreader structure.

To create a sufficiently sturdy spreader structure that is also suited as a filter basket, it is particularly advantageous to provide a total of six spreader rods that are evenly distributed over the circumference of the spreader structure.

It is particularly advantageous if a filter membrane is arranged between at least two spreader rods of the spreader structure described in this invention. By means of the radial spreading of the spreader rods, this filter membrane can be made to assume an substantially unfolded state. This creates a filter body that can be adapted to multiple and specific uses and to the often very diverse operating conditions and objectives.

It is of advantage if the filter membrane extends between all adjacent spreader rods, thereby creating in the aggregate a filter or a filter body, respectively, that substantially spans the entire inside cross section of the channel of a hollow organ.

The filter membrane can extend over the entire exterior sheath of the spreader structure described in this invention, or it can be carefully focused to only extend from a distal end section of the spreader structure up to the midsection thereof. Alternatively or additionally, the filter membrane can extend starting from a proximal end section of the spreader structure up to the midsection thereof.

In specific spots, the filter membrane of this invention can have pores of like or different sizes, created by means of bore holes, braided woven strands and/or a net-like structure. However, the filter membrane can also be a completely intact sheath, where particles or the like are held back only between the interior wall of the hollow organ and the radial outer edge of the filter membrane.

It is of advantage if the pore sizes according to this invention range between approximately 50 μm and 100 μm.

It is advisable to fabricate the filter membrane of nitinol, ePTFE, dacron, polyester, polyurethane, polyacrylic, silicone and/or EPDM. These materials are easy to fold and unfold and are well tolerated, yet they are still sufficiently sturdy to provide the desired filter effect for extended periods.

By means of HF-welding, gluing, recasting or hot pressing, the filter membrane can be attached to at least one spreader rod in a particularly cost-effective and firm manner. Alternatively or additionally, the filter membrane can be produced by dipping and/or spraying it onto the exterior of the spreader structure between at least two spreader rods.

The filter membrane referred to above, can contribute to a significant improvement of the spreader structure according to the preamble of Claim 1 even without the features listed in the characteristics of Claim 1. Thus, a spreader structure of this type having a filter membrane, the longitudinal rods of which, however, do not have at least one area in the longitudinal direction that has less flexural stiffness than adjacent areas, along with an accordingly adapted spreader device and the application thereof, likewise represents an object that reflects another aspect of the invention.

In the following, preferred embodiments of a spreader structure according to this invention are more precisely explained with reference to the enclosed schematic drawings:

FIG. 1 shows a top view of a first embodiment of a spreader structure according to the invention;

FIG. 2 shows the lateral view II-II according to FIG. 1;

FIG. 3 shows a perspective view of the spreader structure according to FIG. 1 on a device for expanding and compressing the spreader structure;

FIG. 4 shows a top view of a second embodiment of a spreader structure according to the invention, and FIG. 5 shows the lateral view V-V according to FIG. 4.

FIGS. 1 and 2 show a spreader structure 10, which in the starting position or the position of rest thereof, respectively, assumes an elongate or unextended shape and which can be inserted in hollow organs such as the heart, blood vessels, bile ducts, urinary tract, gastrointestinal tract, uterus and brain ventricles, where it can serve both as a support organ and a miniature trap or filter basket. In addition, the spreader structure 10 can function as a metal electrode, by means of which heat can be introduced into a hollow organ.

The spreader structure 10 is substantially designed as an elongate body with a total of six spreader rods 12 which extend in a longitudinal direction and are evenly distributed over the circumference of the body. It is advantageous to use a design that provides between 2 and 10 spreader rods; of particular advantage is a design using between 4 and 8 spreader rods.

Both ends of the spreader structure 10 have at their center a first connecting section 14 and a second connecting section 16, respectively. The connecting sections 14 and 16 are preferably designed as cylindrical hollow bodies or tubes, to the walls of which the spreader rods 12 are connected.

Radiating from the first connecting section 14, the individual spreader rods 12 each are equipped with a first section 18 that curves radially outward and is followed by an substantially straight section 20. The straight section 20 transitions into a third section or area 22 shaped like a meander, this meander-shape being understood as the shape already previously defined. This section 22 is followed by an substantially straight fourth section 24, which in turn transitions into a curved fifth section 26. The fifth section 26 ends at the second connecting section 16.

The second and fourth sections 20 and 24 are inclined relative to the longitudinal axis at a 20° angle to the longitudinal axis 36. Angles ranging between 10° and 80° are preferred, and angles between 15° and 25° are most preferred for a spreader structure 10 in the elongate or unexpanded form while in the position of rest. This creates an arrangement in which the sum of the lengths of the individual sections 18, 20, 22, 24 and 26 is greater than the distance or, respectively, the interval between the connecting sections 14 and 16 along the longitudinal axis 36.

The position and elastic properties of the individual sections 20 to 26 are influenced by the type and thickness of the material used. In addition, these properties have also been influenced by a focused heat treatment applied to a number of these sections. In other words, this heat treatment has pre-shaped the spreader structure 10 shown into a starting position in which the spreader rods 12 are already pre-bent.

In the embodiment shown, the third section 22 is meander-shaped such that, compared to the adjacent second and fourth sections 20 and 24, it has reduced flexural stiffness. The meander-shape is formed by short curves and short straight lines between them, the cross sections of these straight lines being substantially square. The cross sections of the remaining sections 18, 20, 24 and 26, however, are rectangular, the surface area of their cross sections each being larger than that of the cross section in the third section 22. In the second and fourth sections 20 and 24, the cross section of which is rectangular, the longer side of the rectangle is arranged pointing radially outward.

The meander-shaped section 22 has a total of approximately 10 meanders. It is advantageous to have between 5 and 15 meanders; having between 8 and 12 meanders provides a particular advantage. The third section 22 with reduced flexural stiffness has substantially the same dimensions as the second and fourth sections 20 and 24. Relative to these sections 20, 22 and 24, the curved sections 18 and 26 are short. The amplitude of the meanders of the third section 22 is approximately twice as large as the width of the adjacent sections 20 and 24. It is advantageous for the amplitude to be approximately equal to 1.5 to 2.5 times the width of the adjacent sections 20 and 24. Particularly advantageous is an amplitude of about 1.7 to 2.3 times the width. The thickness of the meanders should preferably be equal to the thickness of the adjacent sections 20 and 24.

The first and second connecting sections 14 and 16 have openings 28 through which a pole or a rod or, respectively, the tube or cannula 30 of an expansion and compression device or of a spreader device 32 can be inserted, as illustrated in FIG. 3. In addition, the connecting sections 14 and 16 preferably have a wall thickness that is greater than the radial thickness of the spreader rods 12.

Starting at the spreader device 32, the rod 30 is attached to the connecting section 14 and is moreover enclosed by a tube 34 that can be pushed against the connecting section 16 or is attached thereto.

Using the spreader device 32, the distance along the longitudinal axis 36 of the spreader structure 10 between the two connecting sections 14 and 16 can be changed, thereby expanding or compressing the spreader structure 10. In the spreader device 32 shown, compressive forces act upon the individual spreader rods 12 between the connecting sections 14 and 16 and crowd these spreader rods 12 together, thereby radially moving the third section 22 toward the exterior and buckling or bending it. The spreader rods 12 are elastically deformed and, when the pressure is reduced or released by the tube 34, they once more move radially inward at their center.

Together, the spreader device 32 and the spreader structure 10 are inserted into a sheath 38, by means of which they can be introduced into a hollow organ. Once inside the hollow organ, the spreader structure 10 is ejected from the sheath 38 by means of the rod 30, so that the spreader structure 10 with the tube 34 can be spread out against the wall of the hollow organ.

Alternatively, the spreader structure can already be expanded while still in the rest position; it can be contracted by means of a device that produces a tensile force between the connecting sections in the longitudinal direction of the spreader structure.

Due to the relatively low flexural stiffness of the third sections 22, these sections are deformed particularly easily and at the same time particularly strongly during the deformation, while the substantially straight and relatively sturdy sections 20 and 24 are barely deformed and are merely swung radially outward or inward in their entirety. For this reason, the spreader rods 12 "buckle" at the third sections 22 during the expansion or compression, allowing them to be bent in their entirety by an angle of up to 180°. The two sections 20 and 24 assume the position illustrated in FIG. 3, in which they substantially extend in parallel. In this position the spreader structure 10 is expanded to the maximum.

FIGS. 4 and 5 illustrate a second embodiment of a spreader structure 10, in which a filter membrane 40 is arranged between each of the spreader rods 12. The filter membrane 40 is designed as a net that is attached to the spreader rods 12 like the fabric covering of an umbrella. In the example shown, the filter membrane 40 is arranged on the inside of the rods and by means of radial expansion of the spreader rods 12 can be made to assume an substantially unfolded state.

The highly versatile filter body thus created can be employed in a focused manner, particularly as a blood particle filter, a trap for foreign bodies or, as a further application, in contrast nephropathy.

Beginning at a distal end section of the spreader structure 10, the filter membrane 40 extends to the midsection thereof.

In the filter membrane 40, braided woven strands 44 in the aforementioned net form pores 42 ranging between about 50 µm and 100 µm in size. These woven strands 44 form a honeycomb structure with hexagonal honeycombs on the plane of the net.

The filter membrane 40 is fabricated of nitinol, ePTFE, dacron, polyester, polyurethane, polyacrylic, silicone or EPDM. These materials are easy to fold and unfold and in particular are sufficiently sturdy to provide the desired filter effect for extended periods.

The filter membrane 40 is attached to the spreader rods 12 in the midsection of the spreader structure 10 by means of HF-welding from inside.

LIST OF REFERENCE CHARACTERS

10 Spreader structure
12 Spreader rods
14 First connecting section
16 Second connecting section
18 First section
20 Second section
22 Third section
24 Fourth section
26 Fifth section
28 Opening
30 Rod
32 Spreader device
34 Tube
36 Longitudinal axis
38 Sheath
40 Filter membrane
42 Pore
44 Woven strand

What is claimed is:

1. A spreader structure for insertion into a hollow organ, said spreader structure comprising:
    an elongated body having a circumference and a longitudinal axis;
    a first connecting section located at one end of the elongated body;
    a second connecting section located at a second end of the elongated body opposite the first connecting section;
    a plurality of spreader rods radiating from the first connecting section, extending substantially along the longitudinal axis of said elongated body to the second connecting section, and distributed over the circumference of the elongated body and wherein the spreader rods are positionable against a wall of the hollow organ by means of radial expansion, wherein said spreader rods contain a non-linear segment having inner and outer surfaces, wherein the non-linear segment comprises substantially alternating curved sections at the inner and outer surfaces when in a collapsed state; and
    at least one area of said spreader rods along the longitudinal axis having reduced flexural stiffness in comparison to adjacent areas thereto.

2. The spreader structure according to claim 1, wherein the at least one area having reduced flexural stiffness has a reduced cross sectional area.

3. The spreader structure according to claim 1, wherein the at least one area having reduced flexural stiffness has a non-linear rod section.

4. The spreader structure according to claim 1, wherein the at least one area having reduced flexural stiffness has a meander-shaped rod section.

5. The spreader structure according to claim 1, wherein the at least one area having reduced flexural stiffness has a wave-shaped rod section.

6. The spreader structure according to claim 1, wherein the at least one area having reduced flexural stiffness has a zig-zag-shaped rod section.

7. The spreader structure according to claim 1, wherein the at least one area having reduced flexural stiffness has a square cross section.

8. The spreader structure according to claim 1, wherein the first and second connecting sections are designed as central hubs of the spreader rods in the area of the longitudinal axis.

9. The spreader structure according to claim 1, wherein at least one of the connecting sections has an opening through which a central rod can be slid through to the other connecting section.

10. The spreader structure according to claim 1, wherein the first and second connecting sections are substantially cylindrical.

11. The spreader structure according to claim 1, wherein each of the spreader rods, starting from the first connecting section, has a first section that radially curves outward as well as a subsequent substantially straight second section.

12. The spreader structure according to claim 1, wherein the plurality of spreader rods comprises six spreader rods evenly distributed over the circumference.

13. A method of using a spreader structure for insertion into a hollow organ, the method comprising:
    providing an elongated body having a plurality of spreader rods extending evenly from around the elongated body, wherein the spreader rods each have at least one area of reduced flexural stiffness in comparison to adjacent areas, further wherein said spreader rods contain a non-linear segment having inner and outer surfaces, wherein the non-linear segment comprises substantially alternating curved sections at the inner and outer surfaces when in a collapsed state;
    positioning the elongated body on a spreader device;
    inserting the elongated body and spreader device into the hollow organ while the elongated body is at least partially compressed; and
    expanding the elongated body.

14. The method of claim 13, further comprising:
    placing the elongated body inside a sheath while being at least partially compressed;
    inserting the sheath into the hollow organ;
    ejecting the elongated body from the sheath; and
    expanding the elongated body.

* * * * *